United States Patent [19]

Hashimoto et al.

[11] Patent Number: 5,700,944

[45] Date of Patent: Dec. 23, 1997

[54] PROCESS FOR THE PRODUCTION OF PYRIDINECARBOXYLIC ACIDS

[75] Inventors: Toshihiro Hashimoto; Kenichi Nakamura; Makoto Takagawa, all of Tsukuba, Japan

[73] Assignee: Mitsubishi Gas Chemical Company, Tokyo, Japan

[21] Appl. No.: 646,631

[22] Filed: May 8, 1996

[30] Foreign Application Priority Data

| May 19, 1995 | [JP] | Japan | 7-121681 |
| May 19, 1995 | [JP] | Japan | 7-121682 |
| Jan. 26, 1996 | [JP] | Japan | 8-011797 |
| Jan. 26, 1996 | [JP] | Japan | 8-011798 |

[51] Int. Cl.$^6$ .................................................. C07D 213/807
[52] U.S. Cl. ..................................... 546/327; 546/326
[58] Field of Search ..................................... 546/326, 327

[56] References Cited

U.S. PATENT DOCUMENTS 3,801,584  4/1974  Kubo et al. .......................... 546/326

FOREIGN PATENT DOCUMENTS

93/050022  3/1993  WIPO ............................... 546/326

*Primary Examiner*—Zinna Northington-Davis
*Attorney, Agent, or Firm*—Wenderoth, Lind & Ponack

[57] ABSTRACT

A process for the production of a pyridinecarboxylic acid by the air-oxidation of an alkylpyridine in a liquid phase, in which the conversion of the alkylpyridine is high, the yield of the pyridinecarboxylic acid is therefore high, the content of impurities in the product is decreased, and unreacted raw material and an oxidation intermediate can be recycled without the adverse effect of accumulation of the catalyst and bromine component, the process comprising oxidizing an alkylpyridine with an oxygen-containing gas in a solvent in the presence of a catalyst formed of a heavy metal salt and a bromine compound, the solvent being a lower aliphatic monocarboxylic acid having a water content of 2 to 15% by weight, or the process comprising the step of catalytically hydrogenating an oxidation reaction mixture or an isolated pyridinecarboxylic acid in the presence of a catalyst of a metal belonging to the group VIII of the periodic table.

16 Claims, No Drawings

PROCESS FOR THE PRODUCTION OF
PYRIDINECARBOXYLIC ACIDS

FIELD OF THE INVENTION

The present invention relates to a process for the production of pyridinecarboxylic acids useful as raw materials for feed additives and medicines.

PRIOR ART OF THE INVENTION

As an industrial method of producing a pyridinecarboxylic acid by directly oxidizing alkylpyridine, there is known a method in which alkylpyridine is catalytically oxidized in a gaseous phase in the presence of a catalyst or a method in which alkylpyridine is oxidized in a liquid phase in the presence of nitric acid as an oxidizing agent.

The catalytic oxidation in a gaseous phase has a problem in that the selectivity to, and the yield of, a pyridine carboxylic acid are low. The oxidation with nitric acid has a problem in that a large amount of nitric acid is required and that undesirable by-products are formed.

For overcoming the above problems, there has been proposed an air oxidation method in a liquid phase in the presence of a heavy metal catalyst. For example, Japanese Patent Publication No. 9868/1959 discloses a method of producing a pyridinecarboxylic acid in which alkylpyridine is oxidized in a lower aliphatic carboxylic acid as a solvent in the presence of cobalt, manganese and bromine. However, this method is a defect in that the conversion is low.

JP-A-55674/1974 discloses a method in which a large amount of cobalt as a catalyst is used for increasing the yield of pyridinecarboxylic acid. It is, however, industrially difficult to use a large amount of cobalt as a catalyst.

JP-B-17068/1975 (U.S. Pat. No. 3,801,584) discloses a method in which a zirconium catalyst is used in combination with cobalt, manganese and bromine for improving the conversion of alkylpyridine and the yield of pyridinecarboxylic acid. In an industrial process, however, it is a precondition that the catalyst and a reaction mother liquor should be recycled. It is therefore disadvantageous in view of an industrial process to use different elements as catalysts.

JP-A-221741/1991 discloses a method in which chlorine is added as a catalyst in addition to cobalt, manganese and bromine. In this case, however, the catalyst system is also complicated, and the use of a large amount of highly corrosive chlorine as a catalyst is disadvantageous in view of an industrial process.

The above conventional methods of producing pyridinecarboxylic acid by air-oxidizing alkylpyridine in a liquid phase in the presence of heavy metal catalysts have problems as described above, and none of these methods have been established as an industrially accepted production method.

The present inventors have made diligent studies and have succeeded in providing an industrially advantageous method of producing pyridinecarboxylic acid by oxidizing alkylpyridine in a liquid phase, in which the conversion of the alkylpyridine is high and the yield of the pyridinecarboxylic acid is high.

However, the above pyridinecarboxylic acid production method still has a problem in that impurities including bromine are contained in the pyridinecarboxylic acid as an end product. A crude pyridinecarboxylic acid obtained by air oxidation in a liquid phase generally contains nonionic bromine in an amount of several tens to several hundreds ppm. For use of pyridinecarboxylic acid for feed and medicines, it is required to remove the above impurities.

However, little is known with regard to the purification of pyridinecarboxylic acid. For example, Japanese Patent Publication No. 16737/1962 discloses a purification method based on sublimation. However, the sublimation-based purification method is not efficient for purifying pyridinecarboxylic acid of which the problem is a very small content of impurities.

The present inventors have therefore studied and succeeded in providing a method of decreasing bromine impurities by industrially advantageously purifying a crude pyridinecarboxylic acid isolated from an oxidation reaction mixture obtained by oxidizing alkylpyridine in a liquid phase. That is, in this method, the crude pyridinecarboxylic acid isolated from an oxidation reaction mixture obtained by oxidizing alkylpyridine in a liquid phase is catalytically hydrogenated in the presence of a catalyst of a metal belonging to the group VIII of the periodic table, whereby impurities containing bromine are decreased.

In the above method, however, it is required, after the oxidation, to isolate a crude pyridinecarboxylic acid and it is required to dissolve the crude pyridinecarboxylic acid in a solvent to purify it. The above method therefore has a problem in that the process is complicated since it is required to isolate the pyridinecarboxylic acid twice after the oxidation.

Therefore, the present inventors have made further studies, and have found that impurities (including bromine) in a pyridinecarboxylic acid obtained by the oxidation can be decreased to a great extent by a method in which the oxidation reaction mixture is catalytically hydrogenated in the presence of a catalyst of a metal of the group VIII without isolating the crude pyridinecarboxylic acid. The above method requires no step of isolating the crude pyridinecarboxylic acid from the oxidation reaction mixture, that is, it is sufficient to carry out the precipiation of a crystal once. The above method is therefore greatly advantageous in view of an industrial process.

For carrying out the above method industrially advantageously, it is required to recycle unreacted material in the oxidation reaction mixture and formed product, oxidation intermediate and the catalyst of an expensive heavy metal which are all disolved in the solvent after the pyridinecarboxylic acid is isolated. For easily complying with the above requirement, it is conceivable to recycle the reaction mixture from which the pyridinecarboxylic acid has been isolated, to the oxidation.

The present inventors' study shows the following. When the reaction mixture from which the formed pyridinecarboxylic acid has been isolated is recycled to the oxidation simply, i.e., without any treatment, it is particularly required to add a large amount of a bromine component in order to achieve a result equivalent to that of the first oxidation. As a result, with an increase in the number of the recycling of reaction mixture, the bromine concentration in the reaction mixture increases, which affects the quality of the pyridinecarboxylic acid as an end product, the concentration of an organic bromide in particular.

JP-A-233150/1995 discloses a method in which unreacted raw material and oxidation intermediate are recycled together with a catalyst in the solvent-free autoxidation of 3-methylpyridine in a liquid phase. In Examples where the oxidation reaction mixture from which nicotinic acid has been separated is directly recycled, a large amount of a catalyst is added, and in particular, a bromine component is added in an amount equivalent to that used in the first reaction. The above accumulation of the bromine component causes an undesirable effect as the recycling process is repeated many times.

As explained above, for recycling the catalyst-containing reaction mixture in the conventional method of oxidation of alkylpyridine in a liquid phase, it is required to add a large amount of the catalyst component, and the accumulation of the catalyst is a problem. According to the present invention, there is provided an industrially advantageous process for the production of a pyridinecarboxylic acid, which can overcome the above various problems of the conventional methods. The above object of the present invention will be more specifically apparent from the following description.

SUMMARY OF THE INVENTION

It is an object of the present invention to provide a process for the production of a pyridinecarboxylic acid by the air-oxidation of an alkylpyridine in a liquid phase, in which the conversion of the alkylpyridine is high and the yield of the pyridinecarboxylic acid is therefore high.

It is another object of the present invention to provide a process for the industrially advantageous purification of a crude pyridinecarboxylic acid obtained by the air-oxidation of an alkylpyridine in a liquid phase, in order to decrease bromine impurities.

It is further another object of the present invention to provide a process in which an oxidation reaction mixture containing a catalyst, unreacted raw material and an oxidation intermediate can be recycled without the adverse effect of accumulation of the catalyst and bromine component in order to enable the advantageous industrial practice of the air-oxidation of an alkylpyridine in a liquid phase.

According to the present invention, there is provided a process for the production of a pyridinecarboxylic acid, comprising oxidizing an alkylpyridine with an oxygen-containing gas in a solvent in the presence of a catalyst formed of a heavy metal salt and a bromine compound, the solvent being a lower aliphatic monocarboxylic acid having a water content of 2 to 15% by weight.

According to the present invention, further, there is provided a process for the production of a pyridinecarboxylic acid by oxidizing an alkylpyridine with an oxygen-containing gas in a solvent in the presence of a catalyst formed of a heavy metal salt and a bromine compound, to obtain an oxidation reaction mixture, and isolating a pyridinecarboxylic acid from the reaction mixture, the process comprising the step of catalytically hydrogenating the oxidation reaction mixture or the isolated pyridinecarboxylic acid in the presence of a catalyst of a metal belonging to the group VIII of the periodic table.

According to the present invention, the above process further comprises recycling the oxidation reaction mixture to the step of oxidizing an alkylpyridine after the pyridinecarboxylic acid is isolated therefrom.

According to the present invention, the above process further comprises catalytically hydrogenating the oxidation reaction mixture after the pyridinecarboxylic acid is isolated therefrom and then recycling the resultant oxidation reaction mixture to the step of oxidizing an alkylpyridine.

DETAILED DESCRIPTION OF THE INVENTION

The present inventors have made diligent studies concerning the production of a pyridinecarboxylic acid by the oxidation of an alkylpyridine in a liquid phase, and as a result have arrived at the present invention by finding the following. In oxidizing an alkylpyridine in the presence of a catalyst formed of a heavy metal salt such as cobalt or manganese salt, a pyridinecarboxylic acid can be produced at high yields with high conversions in an industrially workable catalyst concentration by the use of a lower aliphatic monocarboxylic acid as a solvent.

That is, according to the present invention 1, there is provided a process for the production of a pyridinecarboxylic acid, comprising oxidizing an alkylpyridine with an oxygen-containing gas in a solvent in the presence of a catalyst formed of a heavy metal salt and a bromine compound, the solvent being a lower aliphatic monocarboxylic acid having a water content of 2 to 15% by weight.

The alkylpyridine used in the present invention refers to a nitrogen-containing heterocyclic compound such as pyridine or a nitrogen-containing aromatic heterocyclic compound such as quinoline, which contains at least one alkyl group as a side chain. The alkyl group includes alkyl groups having 1 to 10 carbon atoms such as methyl, ethyl, n-propyl, i-propyl, n-butyl, i-butyl, n-pentyl, n-hexyl, n-heptyl, i-heptyl, n-octyl, i-octyl, n-nonyl, i-nonyl, n-decyl and i-decyl.

In particular, preferred are 3-methylpyridine and 4-methylpyridine which can be raw materials for nicotinic acid and isonicotinic acid.

Cobalt salt and manganese salt are used as heavy metals for the catalyst. The cobalt salt includes cobalt acetate, cobalt formate, cobalt naphthenate, cobalt bromide, cobalt acetyl acetonate and cobalt carbonate. The concentration of cobalt atom based on the alkylpyridine is in the range of from 0.02 to 1.5% by weight, preferably 0.15 to 0.5% by weight. The manganese salt includes manganese acetate, manganese formate, manganese napthenate, manganese bromide, manganese acetyl acetonate and manganese carbonate. The concentration of manganese atom based on the alkylpyridine is in the range of from 0.02 to 1.5% by weight, preferably 0.15 to 0.5% by weight.

The bromine compound used as part of the catalyst includes sodium bromide, hydrobromic acid, bromine, cobalt bromide, manganese bromide, ammonium bromide, tetrapropylammonium bromide and bromoacetic acid. The concentration of bromine atom based on the alkylpyridine is in the range of from 0.02 to 3% by weight, preferably 0.1 to 1.5% by weight.

The oxygen-containing gas used for the oxidation in a liquid phase includes pure oxygen and a gas mixture containing oxygen and other inert gas, such as air.

The reaction temperature for the oxidation in a liquid phase is 150° to 250° C., preferably 180° to 230° C.

The reaction pressure is defined so as to keep the solvent in a liquid phase, and it is generally 10 to 30 kg/cm$^2$G.

The lower aliphatic monocarboxylic acid used as the solvent includes lower aliphatic saturated carboxylic acids having 2 to 7 carbon atoms such as acetic acid, propionic acid, n-butyric acid, n-valeric acid, n-caproic acid and n-enathic acid.

The water content of the above lower aliphatic monocarboxylic acid is 2 to 15% by weight, preferably 3 to 10% by weight. The amount of the lower aliphatic carboxylic acid having the above water content as a solvent is 3 to 15 times, preferably 5 to 10 times, the weight of the alkylpyridine. In both cases when the water content of the solvent is less than 2% by weight and when the water content of the solvent is greater than 15% by weight, the yield of a pyridinecarboxylic acid and the conversion of the alkylpyridine are low.

When the amount of the solvent is smaller than 3 times the weight of the alkylpyridine, the yield and the conversion are also low.

Therefore, high yields and high conversions are obtained only when a lower aliphatic monocarboxylic acid having a water content of 2 to 15% by weight is used in an amount which is at least 3 times the weight of the alkylpyridine.

When the amount of the solvent is greater than 15 times the weight of the alkylpyridine, neither the yield nor the conversion decreases. However, the amount of the pyridinecarboxylic acid to be obtained is decreased relative to a reactor having a limited capacity, i.e., the production efficiency is decreased. Further, since pyridinecarboxylic acid is soluble in a lower carboxylic acid solvent to some extent, there is another problem in that the pyridinecarboxylic acid is obtained only after a major part of the solvent is evaporated off after the reaction.

It is generally known that a lower aliphatic monocarboxylic acid is used as a solvent in air-oxidation in a liquid phase. For example, acetic acid is used as a solvent for the oxidation of an alkylbenzene such as p-xylene in a liquid phase. However, it is also known that with an increase in the water content of the solvent, the oxidation is more affected and that the yield is low, or the amount of impurities increases, when the solvent contains water as compared with those when the solvent is free of water. In contrast, it has not at all been expected that, when an alkylpyridine is oxidized, a solvent having a water content to some extent can serve to give higher yields than a solvent free of water.

It is not clear what causes the above favorable results. However, for example, nicotinic acid has a higher solubility in a mixture of acetic acid and water than that in acetic acid alone or water alone. On the basis of this behavior in solubility, it is assumed that the use of acetic acid containing water to some extent provides a favorable environment for the solvation state of a pyridinecarboxylic acid as compared with the use of acetic acid alone.

Further, for more effectively producing the above effect of the solvent, it is effective to increase the ratio of the solvent relative to the alkylpyridine. For example, the yield when the amount of the solvent is 6 times the amount of the alkylpyridine is greatly improved over the yield when the amount of the solvent is 3 times the amount of the alkylpyridine.

The use of acetic acid containing water is not only advantageous for improving the yield of the pyridinecarboxylic acid but also advantageous in view of an industrial process. That is, generally, acetic acid used for an oxidation is distilled and recycled, and it is required to separate the acetic acid from water formed during the oxidation. The water content of acetic acid containing water can be adjusted to a proper water content much more easily than the water content of acetic acid free of water, and it is therefore industrially advantageous to use acetic acid containing water as a solvent.

According to the present invention 2, there is provided a process for the production of a pyridinecarboxylic acid by oxidizing an alkylpyridine with an oxygen-containing gas in a solvent in the presence of a catalyst formed of a heavy metal salt and a bromine compound, to obtain an oxidation reaction mixture, and isolating a pyridinecarboxylic acid from the reaction mixture, the process comprising the step of catalytically hydrogenating the oxidation reaction mixture or the isolated pyridinecarboxylic acid in the presence of a catalyst of a metal belonging to the group VIII of the periodic table.

That is, one aspect of the present invention 2 is directed to a process for the production of a pyridinecarboxylic acid, in which a crude pyridinecarboxylic acid obtained by oxidizing an alkylpyridine in a liquid phase is catalytically hydrogenated in the presence of a catalyst of a metal belonging to the group VIII of the periodic table, preferably at a temperature of from 100° to 250° C.

The above process enables the reduction of bromine impurities to such an extent that the influence of the bromine impurities can be almost ignored, and at the same time, the above process can provide a pyridinecarboxylic acid improved in hue as a product.

The metal belonging to the group VIII of the periodic table, used as a catalyst in the present invention, includes metals such as cobalt, nickel, ruthenium, rhodium, palladium, osmium, iridium and platinum and oxides of these metals. Palladium is particularly preferred.

Any one of the above metals or metal oxides may be directly used as a catalyst, while it is generally preferred to use it as a catalyst supported on a carrier. The carrier is selected from activated carbon, silica, alumina and silica-alumina, and activated carbon is particularly preferred.

The solvent used for the above catalytic hydrogenation is selected from water, acetic acid or a mixture of acetic acid and water. The amount of the solvent is 2 to 20 times, preferably 3 to 10 times, the weight of the crude pyridinecarboxylic acid.

Although depending upon the catalyst activity, the reaction temperature for the catalytic hydrogenation is generally 100° to 250° C., preferably 120° to 180° C. The reaction pressure is set in the range in which the solvent can be maintained in a liquid phase. Generally, the reaction pressure is 1 to 80 kg/cm$^2$G, preferably 5 to 20 kg/cm$^2$G, as a hydrogen pressure. When the reaction temperature is too low, the reduction of bromine impurities is insufficient. When the reaction temperature is too high, the reaction system is put in a high pressure so that an apparatus therefor requires an additional cost and that the operation becomes difficult.

The catalytic hydrogenation may be carried out by any one of a batch method and a continuous method.

The purification of an aromatic carboxylic acid by catalytic hydrogenation is generally known. For example, the reduction of 4-carboxybenzaldehyde (4-CBA), an impurity in terephthalic acid, and the improvement of a hue, are known. However, it is not known to use catalytic hydrogenation for the purification of a pyridinecarboxylic acid.

In the purification of terephthalic acid, 4-CBA is mainly decreased as an impurity, while in the purification of the pyridinecarboxylic acid, an organic bromine compound is decreased as an impurity.

Further, a pyridinecarboxylic acid has a molecule containing a basic pyridine ring, and it is difficult to expect that the pyridinecarboxylic acid shows the same behavior as that of terephthalic acid having a molecule containing a nonpolar benzene ring particularly in a reaction involving the coordination to a transition metal such as hydrogenation with a metal belonging to the group VIII of the periodic table.

Another aspect of the present invention 2 is directed to a process for the production of a pyridinecarboxylic acid by oxidizing an alkylpyridine with an oxygen-containing gas in a solvent in the presence of a catalyst formed of a heavy metal salt and a bromine compound, to obtain an oxidation reaction mixture, and isolating a pyridinecarboxylic acid from the reaction mixture, the process comprising the step of catalytically hydrogenating the oxidation reaction mixture from which the pyridinecarboxylic acid is not isolated, in the presence of a catalyst of a metal belonging to the group VIII of the periodic table.

Although depending upon the catalyst activity, the reaction temperature for the catalytic hydrogenation is generally 100° to 250° C., preferably 120° to 180° C. The reaction pressure is set in the range in which the solvent can be maintained in a liquid phase. Generally, the reaction pressure is 1 to 80 kg/cm$^2$G, preferably 5 to 20 kg/cm$^2$G as a hydrogen pressure. When the reaction temperature is too low, the reduction of bromine impurities is insufficient. When the reaction temperature is too high, the reaction system is put in a high pressure so that an apparatus therefor requires an additional cost and that the operation becomes difficult. The catalytic hydrogenation reactivates the catalyst in the oxidation reaction mixture, and at the same time, the catalytic hydrogenation has an effect on the purification of the pyridinecarboxylic acid by hydrogenating an organic bromine compound contained in the reaction mixture. Therefore, even if the oxidation reaction mixture is catalytically hydrogenated before the isolation of the crude pyridinecarboxylic acid, a fully purified pyridinecarboxylic acid can be obtained.

Further, another aspect of the present invention is directed to a process of using the catalytically hydrogenated oxidation reaction mixture in the step of oxidizing an alkylpyridine.

The reaction mixture obtained by the oxidation is catalytically hydrogenated in the presence of a catalyst of a metal belonging to the group VIII of the periodic table before or after a pyridinecarboxylic acid which is precipitated by cooling the reaction mixture is isolated. Further, the reaction mixture may be catalytically hydrogenated after it is concentrated.

The catalytic hydrogenation not only reactivates the catalyst in the oxidation reaction mixture, but also has an effect on the purification of the pyridinecarboxylic acid. It may be therefore reasonable carry out the above catalytic hydrogenation of the oxidation reaction mixture before the formed pyridinecarboxylic acid is isolated.

It is well known that when ionic bromine such as hydrobromic acid or sodium bromide is used as a bromine source for the liquid-phase oxidation in the presence of a heavy metal and bromine as a catalyst, part of the bromine as a catalyst forms an organic compound during the oxidation and that, when acetic acid is used as a solvent, 1-bromoacetic acid and others are formed.

The above organobromine compounds have low activity as a catalyst for the oxidation of an alkylpyridine in a liquid phase. In particular, when a reaction mixture containing a large amount of the organobromine compounds is recycled, the organobromine compounds show almost no activity.

In contrast, when the oxidation reaction mixture is catalytically hydrogenated according to the process of the present invention, organobromine compounds are almost quantitatively reduced to ionic bromine to exhibit sufficient catalyst activity when the reaction mixture is recycled.

Further, brominated pyridinecarboxylic acid, and the like, are also debrominated by the catalytic hydrogenation to form ionic bromine. Further, other impurities which inhibit the oxidation are decreased by the catalytic hydrogenation. As a result, the reaction mixture can be recycled without adding a large amount of a bromine component.

The present invention 1 provides a process for the production of a pyridinecarboxylic acid, in which the conversion of the alkylpyridine is high and the yield of the pyridinecarboxylic acid is therefore high in the liquid-phase oxidation of an alkylpyridine into a pyridinecarboxylic acid.

In the process of the present invention 1, the reaction can proceed in the presence of a simple catalyst system having a relatively low catalyst concentration, and it is therefore easy to recycle the catalyst. Further, since the catalyst contains water, the catalyst can be recycled remarkably advantageously in industry.

The present invention 2 provides a process for the production of a pyridinecarboxylic acid, in which the content of bromine impurities is remarkably decreased, and at the same time the pyridinecarboxylic acid as a product is improved in hue, by catalytically hydrogenating a crude pyridinecarboxylic acid obtained by the oxidation of an alkylpyridine in a liquid phase.

In the process of the present invention 2, the oxidation reaction mixture obtained by the oxidation of an alkylpyridine in a liquid phase is catalytically hydrogenated in the presence of a catalyst of a metal belonging to the group VIII of the periodic table, whereby bromine compounds are decreased as much as bromine compounds are decreased when a crude pyridinecarboxylic acid isolated from the oxidation reaction mixture is catalytically hydrogenated.

In the process of the present invention 2, the step of isolating a crude pyridinecarboxylic acid can be omitted, so that the loss of a pyridinecarboxylic acid dissolved in a solvent used for the purification can be avoided and that the production steps are simplified. Further, due to the above avoidance of a pyridinecarboxylic acid, the yield of a pyridinecarboxylic acid as an end product increases.

In the process of the present invention 2, the oxidation reaction mixture containing the catalyst can be recycled to the step of the liquid-phase oxidation of an alkylpyridine to a pyridinecarboxylic acid without any great alteration of catalyst conditions or an addition of a large amount of a bromine component as a catalyst. As a result, the reaction mixture can be recycled without the accumulation of the catalyst bromine component in the solvent, which is unavoidable in a conventional method, and a high-quality pyridinecarboxylic acid can be produced remarkably advantageously in industry.

In the present invention 1 and the present invention 2, a high-quality pyridinecarboxylic acid can be produced at high yields by an industrially advantageous process. The process of the present invention can be worked industrially easily, and the present invention has a great industrial significance.

EXAMPLES

The present invention will be explained more specifically with reference to Examples hereinafter, while the present invention shall not be limited by these Examples.

Nicotinic acids obtained in Examples were measured for bromine contents and hue as follows.

Bromide ion derived from mother liquor adhered to a nicotinic acid crystal. A crude nicotinic acid obtained by oxidation was recrystallized from acetic acid having a water content of 5% and being 4 times the weight of the crude nicotinic acid, and then the nicotic acid was analyzed.

Bromine in the nicotinic acid was measured by fluorescence X-ray analysis. A dissolved b value refers to a Hunter scale b value obtained by dissolving 1 part by weight of the nicotinic acid in 10 parts by weight of a 1N sodium hydroxide aqueous solution and measuring the solution in a 10 mm cell with transmitted light with a color difference meter, and shows a hue of the nicotinic acid.

Example 1

An autoclave having a stirrer, a gas introducing tube and a refluxer for generated steam was charged with 50 parts by weight of 3-methylpyridine, 0.76 part by weight of cobalt acetate, 0.54 part by weight of manganese acetate, 2 parts by weight of tetrapropylammonium bromide and 150 parts by weight of acetic acid having a 5 wt % water content as a solvent, and the mixture was continuously stirred at a temperature of 210° C. under a pressure of 25 kg/cm$^2$G with feeding air at a rate of 60Nl (normal liter)/hour. The mixture was allowed to react for about 3 hours until no oxygen absorption was found, and then the reaction mixture was cooled to 0° C. A precipitated nicotinic acid crystal was recovered by filtration, washed with acetic acid and dried to give 43.4 parts by weight of crude nicotinic acid. The mother liquor was analyzed by gas chromatography to show that it contained 6.5 parts by weight of raw material 3-methylpyridine and 9.5 parts by weight of nicotinic acid. The conversion of the 3-methylpyridine was 87.0 mol %, the selectivity to the nicotinic acid was 92.1 mol %, and the yield of the nicotinic acid 80.1 mol %. The crude nicotinic acid had a bromine concentration of 470 ppm and showed a dissolved b value of 5.10.

Comparative Example 1

Example 1 was repeated except that the acetic acid having a 5 wt % water content was replaced with 150 parts by weight of acetic acid free of water, whereby 42.6 parts by weight of a nicotinic acid crystal was obtained. The filtrate contained 13.4 parts by weight of 3-methylpyridine and 7.4 parts by weight of nicotinic acid. The conversion of the 3-methylpyridine was 73.3 mol %, the selectivity to the nicotinic acid was 98.3 mol %, and the yield of the nicotinic acid 72.1 mol %. The conversion and the yield were low in Comparative Example 1 as compared with those in Example 1 using a solvent containing water.

Example 2

The same autoclave as that used in Example 1 was charged with 25 parts by weight of 3-methylpyridine, 0.38 part by weight of cobalt acetate, 0.27 part by weight of manganese acetate, 1 part by weight of tetrapropylammonium bromide and 150 parts by weight of acetic acid having a 5 wt % water content, and the mixture was allowed to react in the same manner as in Example 1 to give 21.7 parts by weight of a crude nicotinic acid crystal. The conversion of the 3-methylpyridine was 93.7 mol %, the selectivity to the nicotinic acid was 99.0 mol %, and the yield of the nicotinic acid 92.8 mol %. The conversion and the yield in Example 2 were improved over those in Example 1 since the solvent was used in a larger amount in Example 2. The crude nicotinic acid had a bromine concentration of 608 ppm and showed a dissolved b value of 5.44.

Comparative Example 2

Example 2 was repeated except that the acetic acid having a 5 wt % water content was replaced with 150 parts by weight of acetic acid free of water, whereby 21.2 parts by weight of a nicotinic acid crystal was obtained. The filtrate contained 0.75 part by weight of 3-methylpyridine and 7.2 parts by weight of nicotinic acid. The conversion of the 3-methylpyridine was 97.0 mol %, the selectivity to the nicotinic acid was 87.7 mol %, and the yield of the nicotinic acid 85.9 mol %. The selectivity was low in Comparative Example 2 as compared with those in Example 2 using a solvent containing water.

Comparative Example 3

Example 2 was repeated except that the acetic acid having a 5 wt % water content was replaced with 150 parts by weight of acetic acid having a 20 wt % water content, whereby 9.3 parts by weight of a nicotinic acid crystal was obtained. The filtrate contained 9.5 parts by weight of 3-methylpyridine and 9.5 parts by weight of nicotinic acid. The conversion of the 3-methylpyridine was 60.8 mol %, the selectivity to the nicotinic acid was 93.8 mol %, and the yield of the nicotinic acid 57.0 mol %. The conversion and the yield were greatly low since the solvent contained too much water.

Example 3

An autoclave having a stirrer, a gas introducing tube and a refluxer for generated steam was charged with 20 parts by weight of the crude nicotinic acid (bromine concentration 470 ppm, dissolved b value 5.10) obtained in Example 1, 1 part by weight of a catalyst prepared by supporting 1% by weight of palladium on activated carbon and 200 parts by weight of water. Hydrogen was introduced and sealed at a pressure of 6 kg/cm$^2$G, and the mixture was continuously stirred at 130° C. for 2 hours. After the reaction, the reaction mixture was filtered at a high temperature to remove the catalyst (activated carbon supporting palladium), and the filtrate was cooled to room temperature. A precipitated nicotinic acid crystal was recovered by filtration, washed with water and dried to give 9.4 parts by weight of purified nicotinic acid. The so-obtained nicotinic acid contained 5 ppm of bromine and showed a dissolved b value of 1.19.

Example 4

The same autoclave as that used in Example 3 was charged with 20 parts by weight of the crude nicotinic acid (bromine concentration 608 ppm, dissolved b value 5.44) obtained in Example 2, 0.5 part by weight of a catalyst prepared by supporting 1% by weight of palladium on activated carbon and 100 parts by weight of water as a solvent, and the crude nicotinic acid was purifed under the same conditions as those in Example 3, to give 11.2 parts by weight of purified nicotinic acid. The so-obtained nicotinic acid was analyzed to show a bromine concentration of 31 ppm and a dissolved b value of 2.03.

Example 5

Example 4 was repeated except that the solvent (water) was replaced with 100 parts by weight of acetic acid containing 20% by weight of water, to give 9.7 parts by weight of purified nicotinic acid. The nicotinic acid had a bromine content of 14 ppm and showed a dissolved b value of 1.55.

Referential Example 1

An autoclave having a stirrer, a gas introducing tube and a refluxer for generated steam was charged with 40 parts by weight of 3-methylpyridine, 0.61 part by weight of cobalt acetate, 0.43 part by weight of manganese acetate, 0.52 part by weight of a 47% hydrobromic acid aqueous solution and 240 parts by weight of acetic acid containing 5% by weight of water (the concentrations of the cobalt, manganese and bromine as elements based on the weight of the solvent were 600 ppm, 400 ppm and 1,000 ppm, respectively). The mixture was allowed to react at a temperature of 210° C. under a pressure of 25 kg/cm²G with feeding air at a rate of 60Nl/hour and with stirring, for about 2.5 hours until no oxygen absorption was found, to give 296 parts by weight of an oxidation reaction mixture. The reaction mixture was analyzed to show a 3-methylpyridine conversion of 92.2% and a nicotinic acid yield of 78.8 mol %.

Example 6

An autoclave having a stirrer, a gas introducing tube and a refluxer for generated steam was charged with 145 parts by weight of the oxidation reaction mixture obtained in Referential Example 1 and 1 part by weight of a catalyst prepared by supporting 1% palladium on activated carbon, and hydrogen was introduced and sealed therein at a pressure of 6 kg/cm²G. The mixture was continuously stirred at a temperature of 130° C. for 2 hours.

The catalyst Pd-C was separated from the resultant reaction mixture by filtration, and part of the solvent was distilled off to prepare 80 parts by weight of the reaction mixture. The reaction mixture was cooled to room temperature, and a precipitated nicotinic acid crystal was isolated by filtration and washed with 10 parts by weight of water twice to replace the adhering solvent with water. The crystal was dried to give 16.8 parts by weight of nicotinic acid. The crystal was analyzed by fluorescence X-ray to show a bromine content of 17 ppm.

Comparative Example 4

135 Parts by weight of the oxidation reaction mixture obtained in Referential Example 1 was cooled to room temperature, and a precipitated nicotinic acid crystal was washed with 10 parts by weight of water twice to replace the adhering solvent with water. The resultant crystal was dried to give 13.9 parts by weight of nicotinic acid. The crystal was analyzed by fluorescence X-ray to show a bromine content of 460 ppm.

Comparative Example 5

10 Parts by weight of the nicotinic acid obtained in Comparative Example 4 was added to 50 parts by weight of acetic acid containing 5% by weight of water. The resultant mixture was charged into an autoclave having a stirrer, a gas introducing tube and a refluxer for generated steam, together with 1 part by weight of a catalyst prepared by supporting 1% palladium on activated carbon, and hydrogen was introduced and sealed therein at a pressure of 6 kg/cm²G. The mixture was continuously stirred at a temperature of 130° C. for 2 hours.

The catalyst Pd-C was separated from the resultant reaction mixture by filtration. The remaining reaction mixture was cooled to room temperature, and a precipitated nicotinic acid crystal was isolated by filtration and washed with 10 parts by weight of water twice to replace the adhering solvent with water. The crystal was dried to give 7.8 parts by weight of nicotinic acid. The crystal was analyzed by fluorescence X-ray to show a bromine content of 23 ppm.

Comparative Example 6

The reaction mixture obtained in Referential Example 1 was cooled to room temperature to obtain a crude nicotinic acid crystal. 20 Parts by weight of the crude nicotinic acid crystal was charged into an autoclave having a stirrer, a gas introducing tube and a refluxer for generated steam, together with 0.5 part by weight of a catalyst prepared by supporting 1% palladium on activated carbon and 100 parts by weight of water, and hydrogen was introduced and sealed therein at a pressure of 6 kg/cm²G. The mixture was continuously stirred at a temperature of 130° C. for 2 hours.

The catalyst Pd-C was separated from the resultant reaction mixture by filtration. The remaining reaction mixture was cooled to room temperature, and a precipitated nicotinic acid crystal was isolated by filtration and washed with water twice to replace the adhering solvent with water. The crystal was dried to give 11.2 parts by weight of nicotinic acid. The crystal was analyzed by fluorescence X-ray to show a bromine content of 31 ppm.

When nicotinic acid is crystallized and washed without particularly purifying the oxidation reaction mixture, the crystal contains a large amount of bromine, e.g., as much as 460 ppm of bromine as shown in Comparative Example 4. In contrast, when nicotinic acid is crystallized and washed after hydrogenation-treating the oxidation reaction mixture, the bromine concentration in the crystal is small, e.g., as small as 17 ppm in Example 6.

In Comparative Examples 5 and 6 in which nicotinic acid is crystallized and separated from the reaction mixture first, then redissolved and hydrogenated, the bromine concentrations in the crystals are 23 ppm and 31 ppm, respectively, and there is almost no difference from that in Example 6.

Referential Example 2

An autoclave having a stirrer, a gas introducing tube and a refluxer for generated steam was charged with 40 parts by weight of 3-methylpyridine, 0.61 part by weight of cobalt acetate, 0.43 part by weight of manganese acetate, 0.52 part by weight of a 47% hydrobromic acid aqueous solution and 240 parts by weight of acetic acid containing 5% by weight of water as a solvent (the concentrations of the cobalt, manganese and bromine as elements based on the weight of the solvent were 600 ppm, 400 ppm and 1,000 ppm, respectively). The mixture was allowed to react at a temperature of 210° C. under a pressure of 25 kg/cm²G with feeding air at a rate of 60Nl/hour and with stirring, for about 2.5 hours until no oxygen absorption was found, to give 296 parts by weight of an oxidation reaction mixture. The reaction mixture was analyzed to show a 3-methylpyridine conversion of 92.2% and a nicotinic acid yield of 78.8 mol %.

290 Parts by weight of the above oxidation reaction mixture and 1 part by weight of a catalyst prepared by supporting 1% palladium on activated carbon were charged into an autoclave having a stirrer, a gas introducing tube and a refluxer for generated steam, and hydrogen was introduced and sealed therein at a pressure of 6 kg/cm²G. The mixture was continuously stirred at 130° C. for 2 hours.

The catalyst Pd-C was separated from the above-obtained reaction mixture by filtration, and part of the solvent was distilled off to prepare 160 parts by weight of the reaction mixture. The reaction mixture was cooled to room temperature, and a precipitated nicotinic acid crystal was isolated by filtration and dried to obtain 36.9 parts by weight of nicotinic acid and 105.9 parts by weight of a filtrate. The filtrate contained 4.4 parts by weight of nicotinic acid, 1.8 parts by weight of 3-methylpyridine, 0.11 part by weight of cobalt, 0.11 part by weight of manganese and 0.24 part by weight of bromide ion.

Example 7

77.7 Parts by weight of acetic acid containing 5% by weight of water, 19.2 parts by weight of 3-methylpyridine, 0.1 part by weight of cobalt acetate and 0.04 part by weight of a 47% hydrobromic acid aqueous solution were added to 45 parts by weight of the filtrate obtained after the isolation of the nicotinic acid in Referential Example 2. In this case, the recycle ratio of the filtrate containing the catalyst was about 83%, and the catalyst was added in such an amount that the total catalyst amount was equivalent to the amount of the catalyst in Referential Example 2 (cobalt 600 ppm, manganese 400 ppm and bromine 1,000 ppm).

The resultant reaction mixture was oxidized in the same manner as in Referential Example 2, and the so-obtained oxidation reaction mixture was analyzed to show a 3-methylpyridine conversion of 82.9% and a nicotinic acid yield of 70.4 mol %.

Example 8

77.7 Parts by weight of acetic acid containing 5% by weight of water, 19.2 parts by weight of 3-methylpyridine, 0.1 part by weight of cobalt acetate and 0.26 part by weight of a 47% hydrobromic acid aqueous solution were added to 45 parts by weight of the filtrate obtained after the isolation of the nicotinic acid in Referential Example 2. In this case, the recycle ratio of the filtrate containing the catalyst was about 83%, and the catalyst was added in such an amount that the total catalyst amount was equivalent to the amount of the catalyst in Referential Example 2 (cobalt 600 ppm, manganese 400 ppm and bromine 1,800 ppm).

The resultant reaction mixture was oxidized in the same manner as in Referential Example 2, and the so-obtained oxidation reaction mixture was analyzed to show a 3-methylpyridine conversion of 88.4% and a nicotinic acid yield of 83.2 mol %.

Comparative Example 7

An autoclave having a stirrer, a gas introducing tube and a refluxer for generated steam was charged with 25 parts by weight of 3-methylpyridine, 0.38 part by weight of cobalt acetate, 0.27 part by weight of manganese acetate, 0.32 part by weight of a 47% hydrobromic acid aqueous solution and 150 parts by weight of acetic acid containing 5% by weight of water as a solvent (the concentrations of the cobalt, manganese and bromine as elements based on the weight of the solvent were 600 ppm, 400 ppm and 1,000 ppm, respectively). The mixture was allowed to react at a temperature of 210° C. under a pressure of 25 kg/cm$^2$G with feeding air at a rate of 60Nl/hour and with stirring, for about 2.5 hours until no oxygen absorption was found, to give 181.2 parts by weight of an oxidation reaction mixture. The conversion of 3-methylpyridine was 92.6% and the yield of nicotinic acid was 86.2 mol %.

The above-obtained reaction mixture was cooled to room temperature, and a precipitated nicotinic acid crystal was isolated by filtration and dried to obtain 19.6 parts by weight of nicotinic acid and 156.6 parts by weight of a filtrate. The filtrate contained 8.9 parts by weight of nicotinic acid and 1.8 parts by weight of 3-methylpyridine.

23.2 Parts by weight of 3-methylpyridine was added to 155 parts by weight of the above filtrate obtained after the isolation of nicotinic acid, and the mixture was oxidized under the same conditions as those in the first reaction. That is, the recycle ratio of the filtrate containing the catalyst was about 100%, and the filtrate which was recycled had the same catalyst concentration as that of the mixture used in the first oxidation reaction.

The resultant reaction mixture was analyzed to show a 3-methylpyridine conversion of 65.6% and a nicotinic acid yield of 47.5 mol %.

Comparative Example 8

An autoclave having a stirrer, a gas introducing tube and a refluxer for generated steam was charged with 25 parts by weight of 3-methylpyridine, 0.38 part by weight of cobalt acetate, 0.27 part by weight of manganese acetate, 0.32 part by weight of a 47% hydrobromic acid aqueous solution and 150 parts by weight of acetic acid containing 5% by weight of water as a solvent (the concentrations of the cobalt, manganese and bromine as elements based on the weight of the solvent were 600 ppm, 400 ppm and 1,000 ppm, respectively). The mixture was allowed to react at a temperature of 210° C. under a pressure of 25 kg/cm$^2$G with feeding air at a rate of 60Nl/hour and with stirring, for about 2.5 hours until no oxygen absorption was found, to give 181.9 parts by weight of an oxidation reaction mixture. The conversion of 3-methylpyridine was 92.7% and the yield of nicotinic acid was 87.4 mol %.

The above-obtained reaction mixture was cooled to room temperature, and a precipitated nicotinic acid crystal was isolated by filtration and dried to obtain 19.1 parts by weight of nicotinic acid and 162.8 parts by weight of a filtrate. The filtrate contained 9.4 parts by weight of nicotinic acid and 1.8 parts by weight of 3-methylpyridine.

23.3 Parts by weight of 3-methylpyridine and 0.32 part by weight of a 47% hydrobromic acid aqueous solution were added to 163 parts by weight of the above filtrate obtained after the isolation of nicotinic acid, and the mixture was oxidized under the same conditions as those in the first reaction. That is, the recycle ratio of the filtrate containing the catalyst was about 100%, and the catalyst concentration was as follows. Based on the solvent, the concentration of cobalt was 600 ppm, the concentration of manganese was 400 ppm, and the concentration of bromine was 2,000 ppm. That is, only the concentration of bromine was twice as high as that in the first oxidation reaction.

The resultant reaction mixture was analyzed to show a 3-methylpyridine conversion of 83.5% and a nicotinic acid yield of 59.3 mol %.

As shown in Comparative Example 7, when the filtrate containing the catalyst is recycled without any catalytic hydrogenation to carry out the oxidation under the same conditions as those in the first reaction, the yield of nicotinic acid greatly decreases. However, as shown in Example 7, when the catalytic hydrogenation is carried out before the filtrate is recycled, the yield of nicotinic acid and the conversion of 3-methylpyridine do not much decrease as compared with those in the first reaction.

Further, as shown in Comparative Example 8 and Example 8, when bromine as a catalyst is added the recycled filtrate, the yield of nicotinic acid and the conversion of 3-methylpyridine are improved. However, the results (conversion and yield of nicotinic acid) in Example 8 in which the catalytic hydrogenation was carried out are excellent over the results in Comparative Example 8 where the catalytic hydrogenation was not carried out. That is, the additional amount of bromine in Comparative Example 8 is 1,000 ppm and the additional amount of bromine in Example 8 is 800 ppm. In Example 8 where a smaller amount of bromine is added, the reaction after the filtrate is recycled gives better results due to the effect of the catalytic hydrogenation.

The above results show that the bromine as a catalyst is reactivated by the catalytic hydrogenation of the filtrate and that it is therefore not required to add a large amount of bromine when the oxidation is carried out after the filtrate is recycled.

What is claimed is:

1. A process for the production of a pyridinecarboxylic acid, comprising oxidizing an alkylpyridine with an oxygen-containing gas in a solvent in the presence of a catalyst formed of a heavy metal salt and a bromine compound, the solvent being a lower aliphatic monocarboxylic acid having a water content of 2 to 15% by weight.

2. A process according to claim 1, wherein the alkylpyridine is pyridine or quinoline having at least 1 alkyl side chain having 1 to 10 carbon atoms.

3. A process according to claim 1, wherein the heavy metal salt is at least one member selected from the group consisting of cobalt salts and manganese salts.

4. A process according to claim 1, wherein the cobalt salt is added in an amount of 0.02 to 1.5% by weight based on the alkylpyridine.

5. A process according to claim 1, wherein the manganese salt is added in an amount of 0.02 to 1.5% by weight based on the alkylpyridine.

6. A process according to claim 1, wherein the bromine compound is at least one member selected from the group consisting of sodium bromide, hydrobromic acid, bromine, cobalt bromide, manganese bromide, ammonium bromide, tetrapropylammonium bromide and bromoacetic acid.

7. A process according to claim 1, wherein the lower aliphatic monocarboxylic acid is a lower saturated aliphatic monocarboxylic acid having 2 to 7 carbon atoms.

8. A process according to claim 1, wherein the lower aliphatic monocarboxylic acid having a water content of 2 to 15% by weight is added in an amount 3 to 15 times as large as the weight of the alkylpyridine.

9. A process for the production of a pyridinecarboxylic acid by oxidizing an alkylpyridine with an oxygen-containing gas in a solvent in the presence of a catalyst formed of a heavy metal salt and a bromine compound, to obtain an oxidation reaction mixture, and isolating a pyridinecarboxylic acid from the reaction mixture, the process comprising the step of catalytically hydrogenating the oxidation reaction mixture or the isolated pyridinecarboxylic acid in the presence of a catalyst of a metal belonging to the group VIII of the periodic table.

10. A process according to claim 9, wherein the isolated pyridinecarboxylic acid is catalytically hydrogenated at a temperature in the range of from 100° to 250° C.

11. A process according to claim 9, wherein the metal belonging to the group VIII of the periodic table is at least one metal selected from the group consisting of cobalt, nickel, ruthenium, rhodium, palladium, osmium, iridium and platinum or an oxides of any one of these metals.

12. A process according to claim 9, wherein the isolated pyridinecarboxylic acid is catalytically hydrogenated in the presence of a solvent containing water, acetic acid or a mixture of water and acetic acid.

13. A process according to claim 12, wherein the solvent is added in an amount 2 to 20 times as large as the weight of the pyridinecarboxylic acid.

14. A process according to claim 9, wherein the oxidation reaction mixture is catalytically hydrogenated at a temperature in the range of from 100° to 250° C.

15. A process according to claim 9, wherein the oxidation reaction mixture catalytically hydrogenated is recycled to the step of oxidizing an alkylpyridine after the pyridinecarboxylic acid is isolated.

16. A process according to claim 9, wherein the oxidation reaction mixture is catalytically hydrogenated after the pyridinecarboxylic acid is isolated and then recycled to the step of oxidizing an alkylpyridine.

* * * * *